United States Patent [19]

Sekiguchi et al.

[11] Patent Number: 5,154,855
[45] Date of Patent: Oct. 13, 1992

[54] EMULSIFIED COMPOSITION

[75] Inventors: Shizuo Sekiguchi, Funabashi; Hiroshi Miyake, Narashino; Haruhiko Toda, Chiba, all of Japan

[73] Assignee: Lion Corporation, Tokyo, Japan

[21] Appl. No.: 611,667

[22] Filed: Nov. 13, 1990

[30] Foreign Application Priority Data

Nov. 14, 1989 [JP] Japan .................................. 1-295283

[51] Int. Cl.$^5$ ..................... B61F 17/00; C07H 13/06; A61K 7/075
[52] U.S. Cl. ..................... 252/312; 424/47; 426/602; 252/356; 252/305
[58] Field of Search ......... 252/312, 356, 305; 426/602; 424/514, 47

[56] References Cited

U.S. PATENT DOCUMENTS 3,231,561  1/1966  Brunelle et al. ............... 260/234
4,565,647  1/1986  Lleanado ....................... 252/354

FOREIGN PATENT DOCUMENTS 0334498   9/1989  European Pat. Off. .
WO88/10147 12/1988  PCT Int'l Appl. .
WO89/01480  2/1989  PCT Int'l Appl. .
WO90/08182  7/1990  PCT Int'l Appl. .

Primary Examiner—Richard D. Lovering
Assistant Examiner—N. Bhat
Attorney, Agent, or Firm—Birch, Stewart, Kolasch & Birch

[57] ABSTRACT

An emulsified composition comprises an oily substance and an emulsifying agent which emulsifies said oily substance in water, characterized in that at least one selected from glucose fatty acid monoesters and alkyl glucoside fatty acid monoesters having 1 to 4 carbon atoms in the alkyl group is used as the emulsifying agent.

13 Claims, No Drawings

EMULSIFIED COMPOSITION

BACKGROUND OF THE INVENTION

This invention relates to an emulsified composition which has excellent emulsification stability and can effectively be used as various emulsified foods, cosmetics and the like.

Various nonionic surface active agents have conventionally been known including ethylene oxide or propylene oxide adducts of higher alcohols glycerol esters such as glycerol fatty acid esters and polyglycerol fatty acid esters, sugar alcohol esters such as sorbitan fatty acid esters, and oligosaccharide esters such as sucrose fatty acid esters and maltose fatty acid esters and many of these nonionic surface active agents are used as emulsifying agents. Of these, sucrose fatty acid esters, glycerol esters such as polyglycerol fatty acid esters, and sorbitan fatty acid esters are widely used because of their relatively excellent emulsifying ability.

However, the emulsifying ability of these nonionic surface active agents is insufficient and therefore nonionic surface active agents giving an emulsified composition having superior emulsification stability are desired.

SUMMARY OF THE INVENTION

An object of this invention is to provide an emulsified composition having excellent emulsification stability.

The inventors have found that glucose fatty acid monoesters and alkyl glucoside fatty acid monoesters having 1 to 4 carbon atoms in the alkyl group, especially those having 8 to 20 carbon atoms in the acyl group, although the content of an acyl group having 8 carbon atoms should be 50% by weight or less of the total amount of the acyl groups as an emulsifying agent can give an emulsifying ability superior to that of nonionic surface active agents such as sucrose fatty acid esters and sorbitan fatty acid esters having conventionally been considered to have relatively good emulsifying ability and remarkably increases the emulsification stability of an emulsified composition comprising fats and oils emulsified in water. Thus this invention was completed.

Although the use of a glucose fatty acid ester as a nonionic surface active agent has conventionally been proposed in International Publication No. WO88/10 glucose fatty acid ester consists of about 40 to 50% by weight of monoester, about 40 to 45% by weight of diester and about 5 to 20% by weight of tri- and higher polyesters and such a glucose fatty acid ester that contains not only monoester but also diester and tri- and higher polyesters has no sufficient effect as an emulsifying agent. In contrast, glucose fatty acid monoesters and alkyl glucoside fatty acid monoesters containing substantially no diester, tri- and polyesters, when used as an emulsifying agent, exhibit excellent emulsifying ability and improve emulsification stability.

Accordingly, this invention provides an emulsified composition comprising an oily substance and an emulsifying agent which emulsifies said oily substance in water, in which at least one selected from glucose fatty acid monoesters and alkyl glucoside fatty acid monoesters having 1 to 4 carbon atoms in the alkyl group is used as the emulsifying agent.

DETAILED DESCRIPTION OF THE INVENTION

In the emulsified composition of this invention, at least one of glucose fatty acid monoesters and alkyl glucoside has fatty acid monoesters having 1 to 4 carbon atoms in the alkyl group is used as emulsifying agents for emulsifying fats and oils in water and it is preferable to use at least one of glucose fatty acid monoester and alkyl glucoside fatty acid monoesters each having an acyl group with 8 to 20 carbon atoms, preferably 8 to 16 carbon atoms. Although the acyl groups of glucose and alkyl glucoside fatty acid monoesters used in the emulsified composition may be the same or different, a glucose or alkyl glucoside fatty acid monoester having an acyl group with 8 carbon atoms (glucose or alkyl glucoside monooctanoate) should not be used singly from the viewpoint of emulsifying ability and should be combined with the other glucose or alkyl glucoside fatty acid monoesters in such a manner that the content of an acyl group with 8 carbon atoms is 50% by weight or less, preferably 30% by weight or less of the total amount of the acyl groups.

As glucose, one produced by hydrolyzing starch such as corn or potato with an acid or enzyme followed by decoloration and purification can be used as a starting material for a glucose fatty acid monoester. Examples of such glucose include dextrose, powdery glucose and granular glucose prescribed by JAS.

The alkyl glucoside having 1 to 6, preferably 1 to 4 carbon atoms in the alkyl group which can be used as a starting material includes one each produced by adding a aliphatic alcohol having 1 to 6 carbon atoms to the above glucose such as 1-methyl glucoside, 1-ethyl glucoside and 1-butyl glucoside. Such alkyl glucosides may be those commercially available from Sterly Co., Ltd.

As fatty acids, any ones each having 8 to 20 carbon atoms can favorably be used irrespective of whether they are natural, synthetic, saturated, unsaturated, straight chain or branched chain ones and either the same fatty acids or different fatty acids may be used in one emulsified composition. Examples of natural fatty acids are saturated and unsaturated linear fatty acids such as caprylic acid, decanoic acid, lauric acid, myristic acid, palmitic acid, stearic acid, linoleic acid, oleic acid, capric acid and undecanoic acid which are produced by hydrolyzing plant and animal oils such as coconut oil, palm oil, tallow oil, rape oil and soybean oil. The synthetic fatty acids which can be used include mixtures of linear and branched fatty acids produced by oxidizing olefin polymers and also include fatty acids derived from microorganisms such as γ-linolenic acid. In addition, the alkyl esters in which the alkyl group has 1 to 8 carbon atoms such as methyl, ethyl and propyl esters of the above fatty acids can be used as lower esters of fatty acids as a starting material.

It is preferable that glucose or alkyl glucoside fatty acid monoesters are synthesized from said starting materials by an ester synthesis using lipase or the like, for example, methods such as a transesterification reaction between a fat and oil used as a starting material and glucose or alkyl glucoside, a transesterification reaction between a lower alcohol ester of a fatty acid and glucose or alkyl glucoside and an ester synthesis from a fatty acid and glucose or alkyl glucoside.

In this invention, it is preferable for achieving the above object of this invention to use a glucose or alkyl glucoside fatty acid monoester containing at least 90% by weight, preferably at least 95% by weight of monoester and from 0.1 to 10% by weight, particularly from 0.2 to 5% by weight of diester. It is preferable that the content of tri- and higher polyesters in the glucose or alkyl glucoside fatty acid monoester be 1% by weight or below, preferably 0.5% by weight or below. However, since all of the above mentioned known methods produce esters containing small amounts of monoesters and large amounts of di, tri- and higher polyesters, fractionation and isolation performed after synthesis in order to obtain monoester may require much labor. Therefore, the method using thermostable lipase which the inventors have previously proposed in Japanese Patent Application No. 210,495/1989 is favorably adopted for producing a monoester.

It is preferable to use glucose or alkyl glucoside fatty acid monoesters having the following general formula and produced by esterifying the 6-position OH group of glucose.

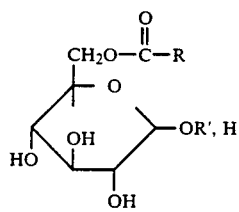

(In the above formula,

represents an acyl group having 8 to 20 carbon atoms and R' represents a hydrogen atom or an alkyl group having 1 to 6 carbon atoms.)

Examples of such glucose fatty acid monoesters include glucose 6-capryl monoester, glucose-6-decane monoester, glucose-6-lauryl monoester, glucose-6-myristyl monoester, glucose-6-palmityl monoester, glucose-6-oleyl monoester and glucose-6-γ-linolate monoester.

Examples of the alkyl glucoside fatty acid monoesters include 1-methyl-6-capryl glucose, 1-ethyl-6-capryl glucose, 1-ethyl-6-lauryl glucose, 1-butyl-6-capryl glucose, 1-ethyl-6-palmityl glucose and 1-ethyl-6-oleyl glucose.

In this invention, the above glucose and alkyl glucoside fatty acid monoesters may be used singly or in combination.

Oily substances emulsified in water in this invention are selected according to the intended use of an emulsified composition and it is possible to use one of hydrophilic fats and oils such as soybean oil and palm oil, hydrophobic fats and oils such as liquid paraffin, wax and vaseline and various other oily substances mentioned later singly or in combination.

The amount of these oily substances used in an emulsified composition, although not specially restricted, is usually within the range of 1 to 90% by weight of the total amount of the composition. The amount of an emulsifying agent (glucose or alkyl glucoside fatty acid monoester) used in emulsifying said oily substances in water can be 0.1 to 20% by weight, especially 0.1 to 10% by weight.

The emulsified composition of this invention, which has excellent emulsification stability due to glucose or alkyl glucoside fatty acid monoesters used as emulsifying agents and also is highly safe, can be used as foods such as dressing, whip cream, mayonnaise and ice-cream and emulsified cosmetics such as creams and milky lotions and can be prepared by a known emulsification or preparation method. In producing the emulsified composition of this invention, proper oily and aqueous ingredients can be used according to the intended use. It is allowed to use other emulsifying agents as long as they do not interfere with the object of this invention. More detailedly, when the emulsified composition of this invention is used as a cosmetic, lipophilic nonionic surface active agents having a HLB of 5.0 or below can be used in addition to the glucose or alkyl glucoside fatty acid monoesters mentioned above. Combined use of the glucose or alkyl glucoside fatty acid monoesters and the lipophilic nonionic surface active agents having a HLB of 5.0 or below results in remarkably increased emulsification stability of an emulsified cosmetic prepared by emulsifying oily substances in water and the resulting emulsified cosmetic is not deemulsified almost entirely even when it is stored at high temperatures for a long period and it has a good affinity to the hair and spreads well on the hair.

It is preferable that the lipophilic nonionic surface active agents used in the emulsified cosmetic have a HLB of 5.0 or below preferably 2.0 to 5.0 and such lipophilic nonionic surface active agents include sorbitan fatty acid esters such as sorbitan sesquistearate, sorbitan tristearate, sorbitan monooleate, sorbitan sesquitol oil fatty acid esters and sorbitan trioleate, POE (6 moles) sorbitol hexastearate, monoglycerides such as glycerylmonostearate and glyceryl monomyristate, propylene glycol fatty acid esters such as propylene glycol monostearate, POE (2 moles) monostearate, POE (2 moles) monooleate, ethylene glycol monostearate, diethylene glycol stearate, POE (2 moles) nonyl phenyl ether, POE (3 moles) castor oil and POE nonyl phenyl formaldehyde condensation products. It is possible to use one of these substances alone or at least two of them in combination.

The amount of the lipophilic nonionic surface active agents used in the emulsified composition is usually 0.05 to 10% by weight, especially 0.1 to 5% by weight of the total amount of the composition.

Although oily substances can be selected according to the types of cosmetics, hydrocarbons having 18 to 60 carbon atoms, fatty acids having 14 to 22 carbon atoms, higher alcohols having 14 to 30 carbon atoms, esters having 16 to 60 carbon atoms, polysiloxanes and the like can be used preferably for hair cosmetics because these oily substances enable the hair to be smoothly combed and can give smoothness and wetness to the hair.

Examples of the above oily ingredients are as follows.
(a) Hydrocarbons having 18 to 60 carbon atoms:
  Liquid paraffin (viscosity: 70 to 350 seconds), squalane ($C_{30}H_{62}$), α-olefin oligomers (polymers of α-olefins having 6 to 20 carbon atoms, mainly trimers), vaseline and the like.
(b) Fatty acids each having 14 to 22 carbon atoms:
  Stearic acid, oleic acid, myristic acid and the like.
(c) Higher alcohols each having 14 to 60 carbon atoms:
  Cetanol, stearyl alcohol, oleyl alcohol, isocetanol and the like.
(d) Esters each having 16 to 60 carbon atoms:
  Isopropyl myristate (IPM), pure cerin, olive oil, castor oil and the like.

(e) Polysiloxanes

Dimethyl polysiloxanes (those having a viscosity of 20 to 3,000,000 cs/25° C. are preferred, including KF-96 produced by Shin-Etsu Chemical Co., Ltd.), methyl phenyl polysiloxanes (KF-56 produced by the same company as above), organopolysiloxanepolyoxyalkylene copolymers (including KF-351, 352 and 610 produced by the same company as above) and the like.

Although the amounts of these oily ingredients used in emulsified compositions are usually 0.05 to 60% by weight, the above ingredients (a) to (d) can be used in amounts of 0.05 to 10% by weight and the above ingredient (e) can be used in an amount of 0.05 to 20% by weight.

Water is used in emulsified cosmetics. The amount of water used in an emulsified cosmetic, although it can be variously changed, is usually 20 to 95% by weight.

Commonly used ingredients can also be used in emulsified cosmetics according to their type and examples of such ingredients are as follows.

(a) Cationic surfactants

Cationic surfactants, when used in hair cosmetics, enable the hair to be smoothly combed and can give smoothness to the hair.

Compounds having the following general formula are suitable as cationic surfactants.

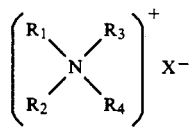

[In the above formula, $R_1$ or $R_1$ and $R_2$ are an alkyl, alkenyl or hydroxyalkyl group having 10 to 24 carbon atoms or a group represented by $-R(OCH_2CH_2)n$ (wherein R is an alkyl or hydroxyalkyl group having 10 to 24 carbon atoms and n is an integer of 1 to 10); $R_2$, $R_3$, and $R_4$ or $R_3$ and $R_4$ are an alkyl group having 1 to 3 carbon atoms, a group represented by

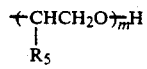

(wherein $R_5$ is a hydrogen atom or a methyl group and m is an integer of 1 to 5), a benzyl group or a cinnamyl group; and X is a halogen atom or an alkylsulfuric acid group having 1 to 2 carbon atoms.]

The amount of the cationic surfactant used in an emulsified cosmetic can be 0.05 to 20%, usually 0.5 to 5% by weight.

(b) Phosphoric esters:

A phosphoric ester is used singly or in combination with the cationic surfactant described in (a) in rinses and the like. The phosphoric ester is usually used in an amount of about 0.1 to 5% by weight and can give good moisture-retaining property and luster to the hair.

Compounds represented by the following general formula are suitable as the phosphoric ester.

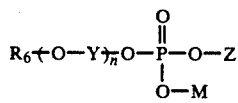

(In the above formula, $R_6$ is a hydrogen atom or a monovalent hydrocarbon group having 5 to 20 carbon atoms; Y is a divalent hydrocarbon group having 2 to 3 carbon atoms; M is a hydrogen atom, an alkali metal or a (hydroxy)alkyl-substituted ammonium group; Z is M or an $R_6-(O-Y)_n$ group; and n is an integer of 0 to 60.)

(c) Hydrophilic alcohols:

Ethanol, glycerol, sorbitol, diethylene glycol, dipropylene glycol, polyethylene glycols, polypropylene polyethylene glycols, hexylene glycol and the like can be used.

(d) pH-adjusting agents:

Organic acids such as citric acid, inorganic acids such as phosphoric acid, inorganic alkalis such as sodium hydroxide, organic amines such as triethanolamine and the like can be used in emulsified cosmetics in order to make them have a pH of 3 to 8 which is close to the physiological pH of scalp.

(e) Water-soluble high molecular compounds

Cationic polymers such as cationic cellulose and Marcoat 550 ®, anionic polymers such as xanthane gum, carrageenan, sulfated cellulose and poly(meth)acrylic copolymers, amphoteric polymers such as Yukaformer ® and chitin, nonionic polymers such as hydroxyethyl cellulose and hydroxyethylated polyacrylic esters and the like can be used in emulsified cosmetics.

(f) Surfactants:

In addition to the above lipophilic nonionic surface active agents, other surfactants can be used in emulsified cosmetics as occasion demands, including nonionic surfactants such as polyoxyethylene sorbitan fatty acid esters, ethylene oxide adducts of glycerol and propylene glycol fatty acid esters, polyethylene glycol fatty acid esters, polyoxyethylene alkyl ethers, polyoxypropylene alkyl ethers, polyoxyethylene alkyl phenyl ethers, polyoxyethylene (hardened) castor oil derivatives, polyoxyalkylamines and polyoxyfatty acid amides, anionic surfactants such as N-acyl amino acid salts and alkylsulfosuccinic acids, and amphoteric surfactants such as lauryl dimethyl aminoacetic acid betaine.

It is also possible to use germicides, anti-dandruff agents, anti-inflammatory agents, hair-growing ingredients, plant extracts, perfumes, pigments and the like in emulsified cosmetics as occasion demands.

The emulsified composition of this invention can be prepared as a hair spray composition and using glucose fatty acid monoesters mentioned above in a hair spray composition containing main hair-conditioning agents and a nonflonic propellant products fine and soft vapor during spraying and can improve vapor properties without raising uncomfortable jet sounds.

Although flonic compounds have conventionally been used frequently as propellants in hair spray compositions, the use of flonic compounds tends to be restricted internationally because they destroy the ozone layer of the earth.

Therefore, various propellants replacing flonic ones have been proposed. However, no propellants for spray-type hair conditioners having at least the same effect as flonic propellants have been found up to now. Specifically, conventional spray-type hair conditioners containing flonic propellants produced soft and fine vapor during spraying and raised relatively soft jet sounds. In contrast, when nonflonic propellants including LPG and dimethyl ether were used in spray-type hair conditioners, they were not favorable in terms of the feel of use because vapors produced during spraying were coarse and devoid of softness and uncomfortable jet sounds were raised.

Nevertheless, the combined use of a nonflonic propellant such as LPG or dimethyl ether and glucose fatty acid esters unexpectedly solves these problems and can achieve specific effects of producing a fine and soft vapor and making the jet sound soft despite the use of a nonflonic propellant.

High molecular substances for fixing the hair and oily substances being liquid at a normal temperature can be used as main hair-conditioning agents. Any ones adhering to the hair and capable of giving hair setting property to hair spray compositions can be used as high molecular substances for fixing the hair. These high molecular substances include polyvinyl pyrrolidones, vinyl acetate-crotonic acid copolymers, copolymers of vinyl acetate, crotonic acid and a vinyl ester which can be copolymerized with vinyl acetate and crotonic acid, vinyl pyrrolidone-vinyl acetate copolymers, maleic anhydride-olefin copolymers, acrylamide-acrylatebutylaminoethylmethacrylate copolymers, hydroxypropyl cellulose and cationic cellulose and one or at least two of these substances can be used in a hair spray composition. It is preferable that the amount of these high molecular compounds used in a hair spray composition is 0.1 to 10%, preferably 0.5 to 5% by weight.

On the other hand, oily substances being liquid at ordinary temperature have both the effect of giving luster to the hair and the effect of making gray hairs inconspicuous. The liquid oily substances including the following ones can be used singly or in combination in a hair spray composition: silicone oils such as dimethyl siloxanes, methyl phenyl siloxanes, polyoxyalkylene-modified silicones, amino-modified silicones and cation-modified silicones; animal and plant oils such as lanolin oil, camellia oil, mink oil, turtle oil, cacao butter, coconut oil, haze wax, beef tallow, hog fat, linseed oil, sunflower oil, cotton seed oil, olive oil and egg yolk oil; ester oils such as isostearyl malate, cholesterol linoleic acid ester, methyl isostearate, isopropyl laurate, cetyl octanoate, isopropyl myristate and isotridecyl myristate; and hydrocarbons such as liquid paraffin, isoparaffin and microcrystalline wax. It is preferable that the amount of one or at least two of these liquid oily substances used in a hair spray composition is 0.01 to 5%, preferably 0.05 to 2% by weight.

It is preferable that in addition to main hair-conditioning agents mentioned above a polyhydric alcohol is used in a hair spray composition in order to give wet luster to the hair. The polyhydric alcohols which can be used in hair spray compositions include glycerol, diglycerol, polyglycerols, propylene glycol, dipropylene glycol, diethylene glycol, polyethylene glycols, methyl glycosides and ethyl glycosides and usually 0.5 to 30% by weight of such a polyhydric alcohol can be used in a hair spray composition.

Although any nonflonic propellants including various hydrocarbons can be used in hair spray compositions, it is preferable to use a hydrocarbon having 3 to 8 carbon atoms, especially LPG and it is also possible to use dimethyl ether, hydrocarbon halogenides or the like.

Such a propellant is used in an amount for adjusting the jet pressure to within a proper range and the ratio by weight of a base liquid to a propellant is usually 10 to 80 : 90 to 20.

The emulsified composition of this invention can also be prepared as a coffee drink, a milk drink, a cocoa drink and a cloudy for drinks.

Coffee drinks

Coffee drinks are prepared by drying and roasting seeds (usually called coffee beans) obtained by rinding berries of coffee trees belonging to the genus cocoa of Rubiaceae and then powdering the roasted coffee beans as occasion demands followed by extracting the powder with hot water and as occasion demands adding sugar and milk ingredients to the resulting supernatant.

Milk drinks

Milk drinks are prepared by mixing a milk such as whole milk, skimmed milk or condensed milk, sugars, an emulsifying agent and the like with water to disperse and dissolve them in it and then pouring the resulting liquid into cases, followed by heating and sterilization.

Cocoa drinks

After cacao beans of cacao trees were parched and flesh obtained by removing the shells of the parched cocoa beans were heated to prepare a cacao paste, it was compressed and defatted and the resulting material was pulverized. A cacao drink is obtained by heating a mixture of sugar, water and the resulting powder usually containing about 20% of fat and then adding water or milk (skimmed milk), followed by stirring and mixing. It is necessary to add an emulsifying agent to the mixture for the emulsification dispersion stability of the fatty substance.

Using glucose fatty acid monoesters mentioned above in such a drink results in its excellent storage stability and taste. Such a drink composition, even when having been stored for a long period, is free from creaming or separation and does not give out any offensive taste or smell. Furthermore, it remains favorably emulsified even when having been stored at high temperatures and is free from so-called neckling in bottling.

The above drink composition can usually be produced by any method. For example, it can be produced by mixing raw materials, heating the mixture while mixing it at 60 to 70° C., further heating the mixture and packing it in prescribed cases, followed by heating or microwave sterilization at 120° C.

Using a polyglycerol fatty acid ester or a sucrose fatty acid ester or both of these as other stabilizers in this drink composition inhibits fat separation during storage and can further prolong the available period of the article of commerce.

The polyglycerol fatty acid ester includes one obtained from a glycerol polymer having an average polymerization degree of about 2 to 15 such as diglycerol, tetraglycerol, hexaglycerol or decaglycerol and a fatty acid having 8 to 20 carbon atoms such as stearic acid, oleic acid, lauric acid, linolenic acid or ricinoleic acid. Regarding the esterification degree of the esterified compound, monoester, triester, pentaester or the like can be used. Examples of the polyglycerol fatty acid monoester include decaglycerol monostearate (commercially available from Sakamoto Chemical Co., Ltd. as the trade name of MSW-750)

It is preferable that the amount of a polyglycerol fatty acid ester used in a drink is within the range of 0.001 to 0.05% by weight of the total amount of the drink. The amount of a polyglycerol fatty acid ester outside of this range may not be able to achieve the purpose of its addition.

A sucrose fatty acid ester represented by the following general formula is used as another stabilizer.

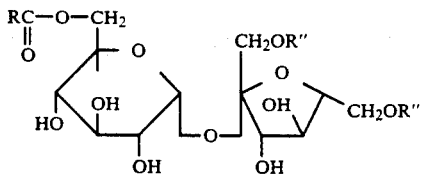

(In the above formula,

represents a fatty acid radical having 8 to 20 carbon atoms; and R" represents

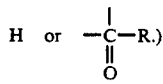

Sucrose fatty acid esters represented by the above general formula include sucrose esters of stearic acid, lanolic acid, palmitic acid and oleic acid. Although the esterification degree of the sucrose fatty acid may be any one such as monoester, diester or triester, it is preferable that the sucrose fatty acid contains at least 70% by weight of monoester.

The amount of the sucrose fatty acid ester used in a drink may preferably be within the range of 0.001 to 0.05% by weight of the total amount of the drink. The amount of a sucrose fatty acid ester outside of this range may not be able to achieve the purpose of its addition.

It is preferable that the amount of glucose fatty acid monoesters used in the above drink composition is 0.001 to 1% by weight of oil component of the drink composition.

A drink cloudy, which is added to drinks, gives them thickness and juiciness while making them stably emulsified and using an oily substance selected from the group consisting of essential oils, oleoresins, edible oils and natural resins jointly with glucose fatty acid monoesters in a cloudy gives drinks excellent emulsification stability and taste. Such a drink cloudy is free from any creaming or separation even after being stored for a long time and drinks containing the drink cloudy are free from any neckling.

Essential oils which can be used in drink cloudies are citrus oils such as orange oil, lemon oil, lime oil, grapefruit oil, tangerine oil, mandrin oil, mandarin orange oil, shaddock oil, summer orange oil, citrus sudachi oil and citron oil, mint oils such as peppermint oil and spice oils such as perilla oil, cinnamon oil, anise oil, onion oil, pepper oil and papurica oil.

Oleoresins which can be used in drink cloudies are mixed perfumes such as grape, peach, apple, banana, melon, pineapple, strawberry, blueberry, almond, milk, yogurt, beef, pork, peanut, coffee, guarana, tangle, whisky and brandy.

The edible oils which can be used in drink cloudies include soybean oil, sesame oil, cotton seed oil, olive oil, peanut oil, rape oil, coconut oil, palm oil, tallow oil and hog oil.

It is possible to add other oily substances including a sucrose ester such as sucrose diacetate hexabutylate, a specific-gravity-adjusting agent such as glycerol or a fatty acid ester and an antioxidant such as tocopherol.

The ingredients which can be added to an aqueous phase include a thickening agent such as carboxymethyl cellulose, a nonionic emulsifying agent other than a sorbitan fatty acid ester and a sucrose monolaurate, an emulsification-stabilizing agent such as propylene glycol, sorbitol or glycerol and a coloring agent such as a natural pigment.

A drink cloudy can be produced by any usual method. Glucose fatty acid monoesters may be added to either an oily ingredient or an aqueous ingredient. For example, an emulsion can be obtained by mixing an oily phase prepared by adding a specific-gravity-adjusting agent such as sucrose acetate isobutylate to an edible oily substance primarily composed of orange oil with an aqueous phase prepared by adding as occasion demands an aqueous solution of a natural gum such as gum arabic, a thickening agent, a coloring agent and the like to water containing glucose fatty acid monoesters using a homomixer.

A drink cloudy is useful for making straight drinks such as fruit juices, drinks containing fruit juice, lactic acid beverages and flavored pops, medical nutritional drinks, juice pressed from bitter oranges and the like to be stably emulsified.

It is preferable that the amount of glucose fatty acid monoesters used in a drink cloudy is 0.01 to 100% by weight of the amount of oily substances to be emulsified. An amount of glucose fatty acid monoesters less than 0.01% by weight of the amount of oily substances used in a drink may result in its insufficient emulsification stability, and an amount of glucose fatty acid monoesters exceeding 100% by weight of the amount of oily substances used in a drink does not further improve its emulsification stability.

The preferred compositions are as follows.

For emulsified cream-type cosmetics such as hair cream, skin cream and the like, the content of an oily substance is preferably from 20 to 60% by weight and the content of the emulsifying agent of the invention is preferably from 0.5 to 10% by weight.

For emulsified lotion-type cosmetics such as emollient lotion, massage lotion, cleansing lotion and the like, the content of an oily substance is preferably from 1 to 20% by weight and the content of the emulsifying agent of the invention is preferably from 0.5 to 5% by weight.

For emulsified spray-type cosmetics such as hair spray and the like, the content of an oily substance is preferably from 0.05 to 5% by weight, the content of the emulsifying agent of the invention is preferably from 0.5 to 30% by weight and the content of a propellent such as LPG and the like is preferably from 5 to 70% by weight.

For emulsified foods such as mayonnaises and dressings, the content of an oily substance such as fats and oils is preferably from 30 to 90% by weight and the content of the emulsifying agent of the invention is preferably from 0.1 to 5% by weight. Vinegar, sugar, salt, spice and other components may be blended thereto.

For emulsified drinks such as coffee drinks, milk drinks, juices and the like, the emulsifying agent of the invention is preferably blended in an amount of 0.001 to 1 part by weight per 100 parts by weight of an oily substance in the drinks. The emulsifying agent can be previously mixed in such an amount to an oily substance before the oily substance is blended into a drink for emulsifying the drink.

Although this invention is specifically described according to Examples in the following, this invention is not restricted to the following Example.

EXAMPLES 1 TO 4, COMPARATIVE EXAMPLES 1 TO 7

After 10 ml of a 0.5% aqueous solution of each surface active agent shown in Table 1 was put in a 30 ml ground stopper test tube, 10 ml of salad oil or liquid paraffin was added to the solution. Next, after the test tube was stoppered and vigorously shaken 30 times, the test tube was allowed to stand at 30° C. for 30 minutes and the volume (ml) of separated water in the test tube was measured.

The results are also given in Table 1.

| | Total | 100.0% |

*The glucose fatty acid monoester contains 93.5% by weight of monoester, 6% by weight of diester and 0.5% by weight of triester.

Emulsified compositions of Examples 5 and 6 both had excellent emulsification stability.

EXAMPLES 7 TO 9, COMPARATIVE EXAMPLES 8 TO 13

O/W-type skin cosmetics having compositions shown in Table 2 were prepared and their emulsification stability and spread on the hair were evaluated by the following methods. The results are also given in Table 2.

Storage stability

TABLE 1

| Surface active agent | Glucose fatty acid monoester having an acryl group at the 6-position* | | | | | Glucose fatty acid diester Acryl group $C_{10}$ | Glucose fatty acid ester [monoester/diester = 50/50] Acryl group $C_{10}$ | Sucrose fatty acid monoester Acryl group | | | Sorbitan fatty acid monoester Acryl group $C_{12}$ |
|---|---|---|---|---|---|---|---|---|---|---|---|
| | Acryl group | | | | | | | | | | |
| | $C_8$ | $C_{10}$ | $C_{12}$ | $C_{15}$ | $C_8/C_{10}$ = 50/50 | | | $C_{12}$ | $C_{12}/C_{15-18}$ = 50/50 | $C_{15-18}$ | |
| Emulsifying ability (ml) — Salad oil | 10 | 2 | 5 | 5 | 4 | 10 | 8 | 7 | 7 | 7 | 10 |
| Emulsifying ability (ml) — Liquid paraffin | 10 | 5 | 5 | 6 | 5 | 10 | 9 | 9 | 8 | 7 | 10 |
| | Comparative Example 1 | Example 1 | Example 2 | Example 3 | Example 4 | Comparative Example 2 | Comparative Example 3 | Comparative Example 4 | Comparative Example 5 | Comparative Example 6 | Comparative Example 7 |

*The glucose fatty acid monoester contains 99.7% by weight of monoester, 0.3% by weight of diester and 0% by weight of triester.

It was confirmed from the results shown in Table 1 that glucose fatty acid monoesters according to this invention which have acyl groups each containing 8 to 20 carbon atoms and wherein the content of an acyl group containing 8 carbon atoms is 50% or less of the total amount of acyl groups have higher emulsifying ability than sucrose fatty acid esters and sorbitan fatty acid esters.

EXAMPLE 5

| Glucose fatty acid monoester ($C_{12}$)* | 10.0% |
|---|---|
| Liquid paraffin | 25.0% |
| Lanolin | 10.0% |
| Isopropyl myristate | 12.0% |
| Perfume, Pigment | Proper amount |
| Water | Balance |

After each prepared sample was packed in a glass tube (the bottom of which was closed with a rubber stopper) having an inner diameter of 3 cm and a height of 20 cm to the height of 18 cm and was then stored at 50° C. for one month, the presence of an upper separated transparent layer was judged.

○: Almost no separation is observed.
x: A separated layer is clearly observed.

Spread on the hair

After a hair bundle of 25 cm length and 10 g weight was moistened and lightly wrung, 2 g of each prepared sample was applied to the root of the bundle and spread of the sample on the hair when the sample was spread with fingers toward the ends of hairs was sensuously evaluated.

○: Very favorably spreads.
Δ: Favorably spreads.
x: Unfavorably spreads.

TABLE 2

| | Composition (%) | Example | | | Comparative Example | | | |
|---|---|---|---|---|---|---|---|---|
| | | 7 | 8 | 9 | 10 | 11 | 12 | 13 |
| Oily phase | Glycerol monostearate (HLB 4.0) | 2.5 | — | 2.5 | 2.5 | 2.5 | 2.5 | — |
| | Sorbitan monostearate (HLB 4.7) | — | 2.5 | — | — | — | — | — |
| | Glucose-6-palmityl monoester *1 | 1.5 | — | — | — | — | — | — |
| | 1-Methyl-glucose-6-oleyl monoester *2 | — | 1.5 | — | — | — | — | — |
| | 1-Ethyl-6-lauryl glucose *3 | — | — | 1.5 | — | — | — | — |
| | POE (80) hardened castor oil (HLB 15.0) | — | — | — | — | — | — | 1.8 |
| | Cetanol | 3.0 | 3.0 | 3.0 | 3.0 | 3.0 | 3.0 | 3.0 |
| | Liquid paraffin | 5.0 | 5.0 | 5.0 | 5.0 | 5.0 | 5.0 | 5.0 |
| | Squalane | 5.0 | 5.0 | 5.0 | 5.0 | 5.0 | 5.0 | 5.0 |

TABLE 2-continued

| | Composition (%) | Example | | | Comparative Example | | | |
|---|---|---|---|---|---|---|---|---|
| | | 7 | 8 | 9 | 10 | 11 | 12 | 13 |
| | Isopropyl palmitate | 3.0 | 3.0 | 3.0 | 3.0 | 3.0 | 3.0 | 3.0 |
| | Stearic acid | | | | 3.0 | 3.0 | | |
| | Propyl p-hydroxybenzoate | 0.1 | 0.1 | 0.1 | 0.1 | 0.1 | 0.1 | 0.1 |
| Aqueous phase | Glycerol | 5.0 | 5.0 | 5.0 | 5.0 | 5.0 | 5.0 | 5.0 |
| | Methyl p-hydroxybenzoate | — | 0.2 | 0.2 | 0.2 | 0.2 | 0.2 | 0.2 |
| | Triethanolamine | — | — | — | 1.0 | 1.0 | — | — |
| | Carboxyvinyl polymer | — | — | — | — | 0.1 | — | — |
| | Purified water | | | | Balance | | | |
| Perfume | | | | | Proper amount | | | |
| | Total | 100 | 100 | 100 | 100 | 100 | 100 | 100 |
| Storage stability | | ◯ | ◯ | ◯ | x | x | x | x |
| Spread on the hair | | ◯ | ◯ | ◯ | Δ | Δ | x | x |

*1 Monoester: 99.7 wt %, Diester: 0.3 wt %, Triester: 0 wt %
*2 Monoester: 94.0 wt %, Diester: 5.5 wt %, Triester: 0.5 wt %
*3 Monoester: 99.9 wt %, Diester: 0.1 wt %, Triester: 0 wt %

EXAMPLES 10 TO 19, COMPARATIVE EXAMPLES 14 TO 17

After hair spray compositions having the following compositions were produced and packed in spray cases, fineness of vapor produced during spraying and jet sounds raised during spraying were evaluated according to the following criteria. The results are shown in respective Examples and Comparative Examples.

Criteria for Evaluation

Fineness of vapor
- ⊙: Very fine
- : Fine
- x: Coarse and not fine

Jet sound raised during spraying
- ⊙: Soft jet sound
- : Not uncomfortable jet sound
- Δ: Slightly uncomfortable jet sound
- x: Very uncomfortable jet sound

EXAMPLE 10

| Base liquid | |
|---|---|
| Amphoteric polymethacrylic ester | 1.5% |
| Isotridecyl myristate | 0.1 |
| Mixture* of glucose-6-capryl monoester and glucose-6-decanyl monoester ($C_8/C_{10}$ = 8/2) | 0.2 |
| Perfume | Trace |
| Absolute ethanol | Balance |
| Propellants | |
| LPG (2.0 kg/cm², 20° C.) | 34 |
| Dimethyl ether | 9 |
| Total | 100.0% |
| Base liquid/propellants ratio by weight | 57/43 |
| Fineness of vapor | ⊙ |
| Jet sound raised during spraying | ⊙ |

*The mixture contains 97.0% by weight of monoester, 3.0% by weight of diester and 0% by weight of triester in total.

EXAMPLE 11, COMPARATIVE EXAMPLE 14

| | Example 11 | Comparative Example 14 |
|---|---|---|
| Base liquid | | |
| Acrylic ester-methacrylic ester copolymer | 2.0% | 2.0% |
| Distearyl dimethyl ammonium chloride | 0.1 | 0.1 |
| Decamethyl cyclopentasiloxane | 0.05 | 0.05 |
| Glucose-6-capryl monoester* | 0.01 | — |
| 1-Methyl-glucose-6-lauryl monoester* | 0.04 | — |
| Perfume | Trace | Trace |
| Absolute ethanol | Balance | Balance |
| Propellants | | |
| LPG (2.0 kg/cm², 20° C.) | 19.2 | 19.2 |
| Dimethyl ether | 28.8 | 28.8 |
| Total | 100.0% | 100.0% |
| Base liquid/propellants ratio by weight | 52/48 | 52/48 |
| Fineness of vapor | ⊙ | x |
| Jet sound raised during spraying | ◯ | Δ |

*The total monoester content is 99.5% by weight and the total diester content is 0.5% by weight.

EXAMPLE 12

| Base liquid | |
|---|---|
| Amphoteric polymethacrylic ester | 2.0% |
| Isotridecyl myristate | 0.2 |
| Decamethyl cyclopentasiloxane | 0.03 |
| Glucose-6-lauryl monoester* | 0.5 |
| Absolute ethanol | Balance |
| Propellant | |
| LPG (2.0 kg/cm², 20° C.) | 40 |
| Total | 100.0% |
| Base liquid/propellants by weight | 60/40 |
| Fineness of vapor | ⊙ |
| Jet sound raised during spraying | ⊙ |

*Monoester: 99.0 wt %, Diester: 1.0 wt %

EXAMPLE 13, COMPARATIVE EXAMPLE 15

| | Example 13 | Comparative Example 15 |
|---|---|---|
| Base liquid | | |
| Amphoteric polymethacrylic ester | 1.5% | 1.5% |
| Isotridecyl myristate | 0.2 | 0.2 |
| Mixture* of 1-methyl-glucose-6-capryl monoester and 1-methyl-glucose-6-decanyl monoester ($C_8/C_{10}$ = 8/2) | 0.8 | — |
| Perfume | Trace | Trace |
| Absolute ethanol | Balance | Balance |
| Propellants | | |
| LPG (2.0 kg/cm², 20° C.) | 60 | 60 |
| Dimethyl ether | 20 | 20 |
| Total | 100.0% | 100.0% |
| Base liquid/propellants ratio by weight | 20/80 | 20/80 |

-continued

|  | Example 13 | Comparative Example 15 |
|---|---|---|
| Fineness of vapor | ○ | x |
| Jet sound raised during spraying | ○ | x |

*The mixture contains 99.0% by weight of monoester and 1.0% by weight of diester.

EXAMPLE 14

| Base liquid | |
|---|---|
| Amphoteric polymethacrylic ester | 1.5% |
| Isotridecyl myristate | 0.1 |
| Mixture* of glucose-6-capryl monoester and glucose-6-decanyl monoester ($C_8/C_{10}$ = 8/2) | 0.2 |
| Perfume | Trace |
| Purified water | Balance |
| Propellant | |
| Dimethyl ether | 40 |
| Total | 100.0% |
| Base liquid/propellant ratio by weight | 60/40 |
| Fineness of vapor | ◎ |
| Jet sound raised during spraying | ◎ |

*The mixture contains 99.7% by weight of monoester and 0.3% by weight of diester.

EXAMPLES 15, COMPARATIVE EXAMPLE 16

|  | Example 15 | Comparative Example 16 |
|---|---|---|
| Base liquid | | |
| Amphoteric polymethacrylic ester | 2.0% | 2.0% |
| Distearyl dimethyl ammonium chloride | 0.1 | 0.1 |
| 1-Methyl-glucose-6-capryl monoester* | 0.1 | — |
| Glucose-6-lauryl monoester* | 0.1 | — |
| Perfume | Trace | Trace |
| Purified water | 5 | 5 |
| 95% ethanol | Balance | Balance |
| Propellants | | |
| LPG (2.0 kg/cm$^2$, 20° C.) | 32 | 32 |
| Dimethyl ether | 8 | 8 |
| Total | 100.0% | 100.0% |
| Base liquid/propellants ratio by weight | 60/40 | 60/40 |
| Fineness of vapor | ◎ | x |
| Jet sound raised during spraying | ○ | Δ |

*The total monoester content is 97.0% by weight and the total diester content is 0.3% by weight.

EXAMPLES 16, COMPARATIVE EXAMPLE 17

|  | Example 16 | Comparative Example 17 |
|---|---|---|
| Base liquid | | |
| Cationic cellulose | 1.0% | 1.0% |
| Isotridecyl myristate | 0.1 | 0.1 |
| Mixture* of glucose-6-capryl monoester and glucose-6-decanyl monoester ($C_8/C_{10}$ = 8/2) | 0.5 | — |
| Lauryl diethanolamide | 3.0 | 3.0 |
| Perfume | Trace | Trace |
| Purified water | Balance | Balance |
| Propellants | | |
| LPG (2.0 kg/cm$^2$, 20° C.) | 50 | 50 |
| Total | 100.0% | 100.0% |
| Base liquid/propellants ratio by weight | 50/50 | 50/50 |
| Fineness of vapor | ○ | x |
| Jet sound raised during spraying | ◎ | x |

*The mixture contains 99.7% by weight of monoester and 0.3% by weight of diester.

EXAMPLE 17

| Base liquid | |
|---|---|
| Cationic cellulose | 1.0% |
| Distearyl dimethyl ammonium chloride | 0.05 |
| Decamethyl cyclopentasiloxane | 0.05 |
| 1-Methyl-glucose-6-capryl monoester* | 0.05 |
| 1-Methyl-glucose-6-lauryl monoester* | 0.05 |
| Perfume | Trace |
| Purified water | 2 |
| 95% ethanol | Balance |
| Propellant | |
| LPG (2.0 kg/cm$^2$, 20° C.) | 50 |
| Total | 100.0% |
| Base liquid/propellants ratio by weight | 50/50 |
| Fineness of vapor | ◎ |
| Jet sound raised during | ○ |

*The total monoester content is 97.0% by weight of monoester and 3.0% by weight of diester.

EXAMPLE 18

| Base liquid | |
|---|---|
| Amphoteric polymethacrylic ester | 1.0% |
| Cationic cellulose | 1.0 |
| Isotridecyl myristate | 0.2 |
| 1-Ethyl-glucose-1-lauryl monoester* | 0.2 |
| Perfume | Trace |
| Absolute ethanol | Balance |
| Propellant | |
| LPG (2.0 kg/cm$^2$, 20° C.) | 32 |
| Dimethyl ether | 8 |
| Total | 100.0% |
| Base liquid/propellants ratio by weight | 60/40 |
| Fineness of vapor | ○ |
| Jet sound raised during | ◎ |

*Monoester: 95.0 wt %, Diester: 4.5 wt %, Triester: 0.5 wt %.

EXAMPLE 19

| Base liquid | |
|---|---|
| Amphoteric polymethacrylic ester | 1.5% |
| Cationic cellulose | 1.0 |
| Distearyl dimethyl ammonium chloride | 0.05 |
| Decamethyl cyclopentasiloxane | 0.05 |
| Glucose-6-capryl monoester* | 0.5 |
| 1-Ethyl-glucose-6-lauryl monoester* | 0.5 |
| Propylene glycol | 1.0 |
| Perfume | Trace |
| Purified water | 10 |
| 95% ethanol | Balance |
| Propellant | |

-continued

| Dimethyl ether | 50 |
|---|---|
| Total | 100.0% |
| Base liquid/propellants ratio by weight | 50/50 |
| Fineness of vapor | ⊙ |
| Jet sound raised during | ○ |

*The total monoester content is 97.0% by weight and the total diester is 3.0% by weight.

EXAMPLE 20

Given amounts of the following raw materials were mixed together.

| Liquid coffee extract | 200 g (10%) |
|---|---|
| Whole dry milk | 40 g (2%) |
| Sugar | 200 g (10%) |
| Glucose-6-lauryl monoester* | 2 g (0.1%) |

*Monoester: 95.0 wt %, Diester: 5.0 wt %

After water was added to these raw materials and they were dissolved in water by mixing, the total amount was adjusted to 200 g. After the thus prepared liquid was heated to 70° C. and stirred with a homomixer for 5 minutes, the liquid was homogenized with a high pressure homogenizer at a pressure of 150 kg/cm$^2$. The resulting liquid was bottled and sterilized by heating at 120° C. for 25 minutes to prepare coffee drinks.

EXAMPLES 21 TO 22, COMPARATIVE EXAMPLES 18 TO 20

Five types of coffee drink were produced in the same manner as in Example 20 except that the following various emulsifying agents were used instead of glucose-6-lauryl monoester.

A quality evaluation test was performed on coffee drinks obtained in the above Examples and Comparative Examples. The results ar shown in Table 3.

The criterion for emulsification stability evaluation was as follows.
(Criterion for the evaluation)
○: Homogeneous
Δ: Slight floating of cream is observed but mixing makes the coffee drink homogeneous.
x: Floating of cream is observed and lumps remains even after mixing.

ative Examples 18 to 20) all have inferior taste and emulsification stability.

EXAMPLE 23

A drink cloudy having the following composition was produced.

| Composition of the cloudy | |
|---|---|
| Orange oil | 7.0% |
| Sucrose acetate isobutylate | 6.0% |
| 1-Methyl-glucose-6-lauryl monoester* | 1.5% |
| 75% Liquid suqar | 85.5% |
| | 100.0% |

*Monoester: 99.5 wt %, Diester: 0.5 wt %

An emulsifying agent (glucose-6-lauryl monoester) was dissolved in 75% liquid sugar and the solution was heated to 60° C. A mixture of orange oil and sucrose acetate isobutylate was added dropwise to the solution while stirring it with a TK homomixer to produce an emulsified cloudy.

The stability of the thus produced cloudy was evaluated by storing it in a constant temperature bath at 40° C. for one month.

After 0.15 ml of the cloudy was added to 200 ml of a syryp having the following composition to produce an orange drink, its stability was evaluated by storing it at room temperature for two months.

| Composition of the syrup | |
|---|---|
| Sugar | 13% |
| Citric acid | 0.3% |
| Vitamin C | 0.03% |
| Sodium citrate | pH adjustment (pH 3) |
| Water | Balance |
| | 100.0% |

EXAMPLES 24 TO 25, COMPARATIVE EXAMPLES 21 TO 23

Cloudies and orange drinks were produced in the same manner as in Example 23 except that different types of emulsifying agent were used and their amounts used were varied and the stability levels of these cloudies and orange drinks were evaluated.

TABLE 3

| | | | Example | | | Comparative Example | | |
|---|---|---|---|---|---|---|---|---|
| | | | 20 | 21 | 22 | 18 | 19 | 20 |
| Liquid coffee extract | | | 10% | 10% | 10% | 10% | 10% | 10% |
| Whole dry milk | | | 2% | 2% | 2% | 2% | 2% | 2% |
| Sugar | | | 10% | 10% | 10% | 10% | 10% | 10% |
| Glucose-6-lauryl monoester* | | | 0.1% | 0.07% | 0.07% | — | — | — |
| Polyglycerol fatty acid ester | | | — | 0.03% | — | 0.1% | — | 0.03% |
| Sucrose fatty acid ester | | | — | — | 0.03% | — | 0.1% | 0.07% |
| Taste (Sensuous test) | | | No offensive taste | No offensive taste | No offensive taste | Medical smell | Harsh | Slightly harsh |
| Emulsifi- | 5° C. | One month later | ○ | ○ | ○ | Δ | Δ | ○ |
| cation | | Three months later | ○ | ○ | ○ | Δ | Δ | ○ |
| stability | 20° C. | One month later | ○ | ○ | ○ | Δ | Δ | ○ |
| | | Three months later | Δ | Δ | Δ | x | x | x |

Polyglycerol fatty acid ester: MSW-750 produced by Sakamoto Chemical Co., Ltd.
Sucrose fatty acid ester: S-1570 produced by Hishito
*Monoester: 99.7 wt %, Diester: 0.3 wt %

As clearly seen from Table 3, drink compositions of Examples 20 to 22 all have excellent taste and emulsification stability. In contrast, drink compositions not containing any glucose fatty acid monoesters (Compar- The evaluation results in these Examples and Comparative Examples are shown in Table 4. The criterion for the evaluation was as follows.

(Criterion for the evaluation)

Emulsification stability

○ : No changes
x: Creaming or separation occurs.

Stability of the orange drink

○ : No changes
x: Neckling occurs.

TABLE 4

| | | Example | | | Comparative Example | | |
|---|---|---|---|---|---|---|---|
| | | 23 | 24 | 25 | 21 | 22 | 23 |
| Composition of the cloudy (%) | Orange oil | 7 | 7 | 7 | 7 | 7 | 7 |
| | Sucrose acetate isobutylate (SAIB) | 6 | 6 | 6 | 6 | 6 | 6 |
| | 7% Liquid sugar | 85.5 | 85.5 | 85.5 | 85.5 | 85.5 | 85.5 |
| | 1-Methyl-glucose-6-lauryl monoester* | 1.5 | 1.0 | 1.0 | — | — | — |
| | Sucrose fatty acid ester | — | 0.5 | — | 1.5 | — | 0.75 |
| | Polyglycerol fatty acid ester | — | — | 0.5 | — | 1.5 | 0.75 |
| Properties | Emulsification stability of the cloudy | ○ | ○ | ○ | x | ○ | ○ |
| | Stability of the orange drink | ○ | ○ | ○ | ○ | x | x |

*Monoester: 95.0 wt %, Diester: 5.0 wt %

As clearly seen from the above table, cloudies of Examples 23 to 25 all have excellent emulsification stability and orange drinks containing these cloudies also have excellent stability. In contrast, cloudies not containing any glucose fatty acid monoesters (Comparative Examples 21 to 23) themselves have inferior emulsification stability or orange drinks containing those cloudies have inferior stability.

What is claimed is:

1. An emulsified composition comprising an oily substance and an emulsifying agent which emulsifies said oily substance in water, said emulsifying agent being at least one selected from the group consisting of glucose fatty acid monoesters and alkyl glucoside fatty acid monoesters having the following general formula:

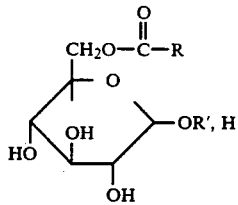

in which

represents an acyl group having 8 to 20 carbon atoms with the proviso that the amount of acyl groups having 8 carbon atoms is 0 to 50% by weight of the total amount of the acyl groups, and $R^1$ represents a hydrogen atom or an alkyl group having 1 to 4 carbon atoms, wherein the monoester content in the glucose fatty acid monoesters or the alkyl glucoside fatty acid monoesters is at least 90% by weight, the diester content is from 0.1 to 10% by weight and the total content of triester and polyesters in the glucose fatty acid monoesters or the alkyl glucoside fatty acid monoesters is 1% by weight or less.

2. The emulsified composition according to claim 1, wherein the glucoside fatty acid monoester has an acyl group having 8 to 16 carbon atoms.

3. The emulsified composition according to claim 1, wherein the amount of acyl groups having 8 carbon atoms is 0 to 30% by weight of the total amount of acyl groups.

4. The emulsified composition according to claim 1, wherein the acyl group is derived from a fatty acid selected from the group consisting of caprylic acid, decanoic acid, lauric acid, myristic acid, palmitic acid, stearic acid, linoleic acid, oleic acid, capric acid and undecanoic acid.

5. The emulsified composition according to claim 1, wherein the monoester content in the glucose fatty acid monoesters or the alkyl glucoside fatty acid monoesters is at least 95% by weight, the diester content is from 0.2 to 5% by weight and the total content of triester and polyesters in the glucose fatty acid monoesters or the alkyl glucoside fatty acid monoesters is 0.5% by weight or less.

6. The emulsified composition according to claim 1, wherein said emulsifying agent is a glucose fatty acid monoester or an alkyl glucoside fatty acid monoester selected from the group consisting of glucose-6-capryl monoester, glucose-6-decane monoester, glucose-6-lauryl monoester, glucose-6-myristyl monoester, glucose-6-palmityl monoester, glucose-6-oleyl monoester, glucose-6-$\gamma$-linoleate monoester, 1-methyl-6-capryl glucose, 1-ethyl-6-capryl glucose, 1-ethyl-6-lauryl glucose, 1-butyl-6-capryl glucose, 1-ethyl-6-palmityl glucose, 1-ethyl-6-oleyl glucose, and combinations thereof.

7. The emulsified composition according to claim 1, wherein said emulsifying agent is a glucose fatty acid monoester selected from the group consisting of glucose-6-capryl monoester, glucose-6-decane monoester, glucose-6-lauryl monoester, glucose-6-myristyl monoester, glucose-6-palmityl monoester, glucose-6-oleyl monoester, glucose-6-$\gamma$-linoleate monoester, and combinations thereof.

8. The emulsified composition according to claim 1, wherein said emulsifying agent is an alkyl glucoside monoester selected from the group consisting of 1-methyl-6-capryl glucose, 1-ethyl-6-capryl glucose, 1-ethyl-6-lauryl glucose, 1-butyl-6-capryl glucose, 1-ethyl-6-palmityl glucose, 1-ethyl-6-oleyl glucose, and combinations thereof.

9. The emulsified composition according to claim 1, wherein said oily substance is selected from the group consisting of hydrophilic fats, hydrophilic oils, hydrophobic fats and hydrophobic oils.

10. The emulsified composition according to claim 1, wherein said oily substance is selected from the group consisting of soybean oil, palm oil, liquid paraffin, wax and vaseline.

11. The emulsified composition according to claim 1, wherein said oily substance is present in an amount of 1 to 90% by weight of the total amount of the composition.

12. The emulsified composition according to claim 1, wherein said emulsifying agent is present in an amount of 0.1 to 20% by weight.

13. The emulsified composition according to claim 1, wherein said emulsifying agent is present in an amount of 0.1 to 10% by weight.

* * * * *